United States Patent [19]

Elliot et al.

[11] Patent Number: 4,623,541
[45] Date of Patent: Nov. 18, 1986

[54] PRODUCTION OF PURIFIED PORCINE IMMUNOGLOBULINS

[75] Inventors: James I. Elliot, Ottawa; Gordon E. Timbers, Nepean; H. Wayne Modler, Kemptville; Robert W. Allen, Carp, all of Canada

[73] Assignee: Candian Patents and Development Limited, Ottawa, Canada

[21] Appl. No.: 748,671

[22] Filed: Jun. 25, 1985

[30] Foreign Application Priority Data

Jun. 26, 1984 [CA] Canada ................................. 457458

[51] Int. Cl.⁴ .................... A61K 35/16; A61K 39/395
[52] U.S. Cl. ..................................... 424/85; 426/647; 426/580; 426/588; 426/657; 530/387; 530/360; 530/365; 530/832; 530/833
[58] Field of Search ............... 426/647, 657, 580, 588; 260/112 B; 424/85

[56] References Cited

U.S. PATENT DOCUMENTS 3,984,539 10/1976 Khouw et al. .............. 260/112 B X
4,096,244 6/1978 Newson et al. ........................ 424/85
4,276,283 6/1981 Eibl et al. ................... 260/112 B X

OTHER PUBLICATIONS

McCallum et al, Can. J. Animal Sci. 57, 151–158 (1978).

Primary Examiner—Howard E. Schain
Attorney, Agent, or Firm—Burke-Robertson, Chadwick & Ritchie

[57] ABSTRACT

A method for the continuous production of a purified immunoglobulin preparation wherein the antibodies are substantially enriched by means of a selective two-step ammonium sulfate fractionation procedure employing centrifugation and ion depletion processes. The purified immunoglobulins are subsequently commingled with condensed skim milk and spray dried. The resulting product for example is employed in the formulation of milk replacers for artificial rearing of neonatal pigs to provide the passive immunity to disease normally provided by sows' colostrum and later milk.

15 Claims, 3 Drawing Figures

FLOW DIAGRAM FOR THE PREPARATION OF
γ-GLOBULIN FORTIFIED MILK REPLACER
SUPPLEMENT

FLOW DIAGRAM FOR THE PREPARATION OF
PURIFIED PORCINE IMMUNOGLOBULINS
ACCORDING TO EXAMPLE I

FLOW DIAGRAM FOR THE PREPARATION OF ENRICHED BOVINE IMMUNOGLOBULINS ACCORDING TO EXAMPLE 2

PRODUCTION OF PURIFIED PORCINE IMMUNOGLOBULINS

The present invention relates to a method for the continuous production of a purified immunoglobulin preparation.

BACKGROUND OF THE INVENTION

The immunoglobulin can be prepared from either porcine or bovine blood collected for example at abattoirs from inspected animals. The preparation from porcine blood has application in the rearing of neonatal pigs while that from bovine blood has potential use in the rearing of calves. The following description is directed primarily to the porcine application.

The neonatal piglet is born without the ability to fight disease and is dependent upon colostral and later milk from the sow to provide immunoglobulins which confer passive immunity to disease for the first 2 to 3 weeks of life. The piglet's endogenous immune system begins to function and produce antibodies in response to environmental stimuli at approximately 2 weeks of age. On an average, 1.5-2.0 pigs per litter of 8-10 are lost between birth and weaning at 3-5 weeks of age as the result of a variety of sow and piglet related factors, including the inability of the piglet to obtain sufficient immunoglobulins from the sows' clostrum. Problems at lactation, extra large litters, within litter competition, poor nursing sows and sow death resulting in partial starvation and weakness leading to chilling and crushing which account for many of these losses. Clearly, a milk replacer imparting the required passive disease immunity would allow piglets to be raised from birth independent of the sow and thereby reduce piglet mortality that is most pronounced during the first 2-4 days of life (Van der Hyde, H. 1972, Proc. Br. Soc. Animal Prod. 33-36).

The availability of a milk based immunoglobulin enriched product which can be used in milk replacer formulation will allow for the rearing of neonatal pigs in a practical environment separate from the dam and allow for populating of new swine units by hysterectomy with pigs that are Specific Pathogen Free (SPF). Traditionally artificial rearing and derivation of SPF pigs was only possible under sterile conditions impractical at the farm level. This system of raising SPF pigs required specialized and expensive equipment. Artificial rearing iof neonatal pigs in a non-isolated or "commercial" environment has met with little success as the piglet is deprived of sow's colostrum and later milk required to provide the immunoglobulins which confer passive immunity to disease-causing and other organisms encountered in a non-isolated environment. A more practical approach would be to surgically remove the piglets from the sow by either caesarean section or hysterectomy and rear them from birth in a "commercial" (non-isolated) environment providing disease resistance from birth by supplementing the milk replacer with porcine immunoglobulins. The weaker pigs in a naturally farrowed litter could be selected soon after birth and reared artificially away from the sow. Those piglets contributing most to the early post-natal mortality could thereby be saved.

Scoot and Coworkers (J. of Animal Science, 1972, Vol. 35, Pages 1201-1205) obtained a survival rate of 75% or more when immunoglobulins were fed for 10 days postpartum to three lots of pigs and this did not differ significantly from control piglets nursing from their dam. Corresponding survival rates of the negative control pigs was 0.33 and 25%. Similar results were obtained by McCallum, Elliot and Owen in 1978 (Can. J. Animal Sci., Vol. 57, Pages 151-158).

The immunoglobulins required to confer passive disease immunity are also present in porcine blood, adequate quantities of which are available in meat packing plants. Currently such porcine blood is processed to produce blood meal. Isolation and concentration of these immunoglobulins from porcine blood has been previously accomplished by cumbersome methods in quantities sufficient to demonstrate that the immunoglobulins so derived can be added to the diet of neonatal pigs removed from the sow at birth and confer upon them the passive immunity to disease which will allow them to survive in a commercial environment, thereby ensuring the success of artificial rearing.

The mechanism by which immunoglobulins can be removed from porcine blood has been a subject of investigation for many years. Methodology employed to-date has been essentially a batch multi-step process which is slow, cumbersome, low yielding and not readily adaptable to commercial production.

Newson (Canadian Pat. No. 1,046,407, 1979) describes a batch process for the production of a product which contains only 20% immunoglobulin. This means that 75-90 g of the product must be fed to meet the suggested first day requirement of 15 g of immunoglobulin: this quantity of material alone already exceeds the daily dry matter requirement of a young pig (67.5 g) and leaves no room for the addition of skim milk powder (SMP) fat, minerals or vitamins. Casein, a normal constituent of SMP (25%), is essential for clot formation in the stomachs of young pigs.

A further method, belonging to the prior art (Eibl. M. Canadian Pat. No. 1,112,166, 1981), describes the preparation of a high purity immunoglobulin (80% pure); however, the method of preparation is extremely long and involved and would not be economically feasible.

SUMMARY OF THE INVENTION

According to the present invention there is provided a method of continuous production of purified porcine or bovine immunoglobulins. An anti-coagulant is first added to collected porcine or bovine blood to preserve it and the cellular fractions are centrifugally removed. Ammonium sulfate is then added to the remaining plasma to obtain a saturation of approximately 20% to 30% to induce fibrin precipitation. The precipitated fibrin is removed by subjecting the plasma to continuous centrifugation. The ammonium sulfate saturation of the plasma is then increased to a range of approximately 35% to 50% and the product is subjected to further centrifugation in order to remove, in the effluent, partially deproteinated immunoglobulins and albumins dissolved therein. The continuously discharged sludge from the centrifugation step, containing the immunoglobulins in the concentrated form is collected, and water is added to redissolve the immunoglobulins. The resultant immunoglobulin solution is subjected to an ion depletion process to remove a major portion of the ammonium sulfate. The purified immunoglobulin product is then subjected to appropriate concentration and treatment for storage (eg. freeze-drying), or is blended with suitable protein sources to provide an appropriate daily intake of immunoglobulins for the intended animal. For example, the immunoglobulin product intended for piglets derived from porcine blood may be blended with condensed skim milk to give a solids ratio of about 1:3 (immunoglobulins/skim milk solids), and the resulting mixture spray dried to yield a pig-milk replacer component which can be reconstituted and fed as required.

The method according to the present invention provides a product which is unexpectedly high in purity and is extremely effective for example, when derived from porcine blood, in the formulation of milk replacers for artificial rearing of neonatal pigs to provide the necessary passive immunity to disease otherwise provided by sows' colostrum and later milk.

BRIEF DESCRIPTION OF THE DRAWINGS

These and other objects and advantages of the invention will become apparent upon reading the following detailed description and upon referring to the drawings in which.

While the invention will be described in conjunction with example embodiments, it will be understood that it is not intended to limit the invention to such embodiments. On the contrary, it is intended to cover all alternatives, modifications and equivalents as may be included within the spirit and scope of the invention as defined by the appended claims. For example, while the invention will be described in conjunction with specific processes for preparing porcine immunoglobulins, it is intended that the invention also extend to bovine immunoglobulins prepared from collected bovine blood.

GENERAL DESCRIPTION OF METHOD ACCORDING TO PRESENT INVENTION

Figure 1:
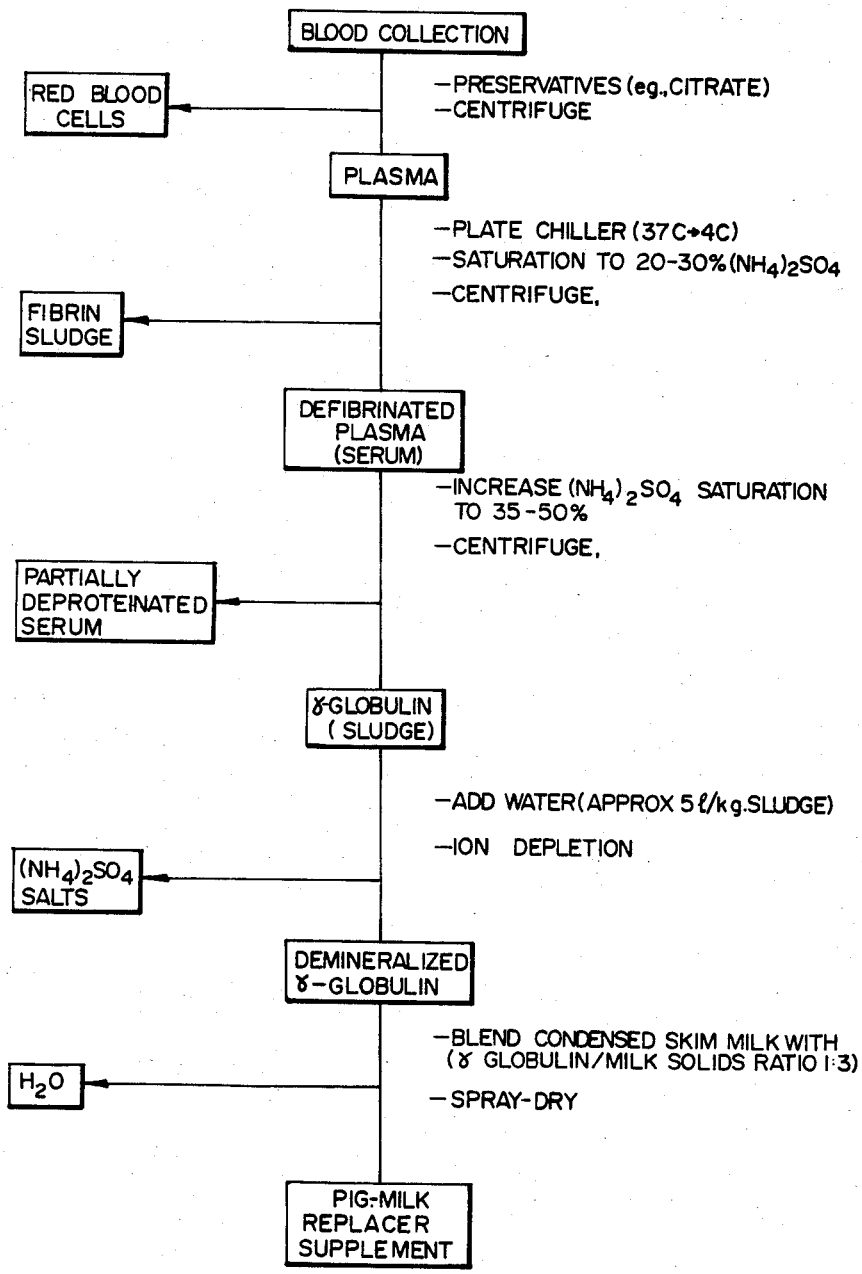
FIG. 1 is a flow diagram for the preparation of a globulin fortified milk replacer supplement according to the process of the present invention.

Purified immunoglobulins according to the present invention are prepared as outlined in the flow diagram of FIG. 1. Blood is collected from a large number of pigs at a government inspected slaughter-house and preserved by the addition of an anti-coagulant, e.g., sodium citrate, to prevent clotting. The cellular fractions (erythrocytes, leukocytes and platelets) are removed centrifugally and account for about a 40% volume reduction, leaving about 60% plasma. The plasma is chilled and ammonium sulfate added to obtain approximately 20%-30% saturation to induce fibrin precipitation. The ammonium sulfate can be added in a batch system or portion metered in-stream on a continuous flow basis to obtain the desired saturation. The precipitated fibrin is removed by subjecting the product to continuous centrifugation. Subsequently, saturation of the ammonium sulfate is increased from the range of 20%-30% to a range of 35% to 50%. The resulting product contains mainly aggregated immunoglobulins which are subjected to an enrichment centrifugation procedure. The albumins, being soluble at this stage, are voided in the effluent stream while the immunoglobulins are concentrated and continuously discharged as a sludge. The sludge is then reconstituted with water being added at a rate of approximately 5/kg of material, following which the redissolved immunoglobulins are subjected to a suitable ion depletion process to remove the ammonium sulfate (e.g., ion exchange, ultrafiltration or electrodialysis).

Upon reduction of ammonium sulfate levels, the purified immunoglobulins may, for example, be further concentrated by way of low temperature evaporation, reverse osmosis or dewatering and freeze-dried for storage for subsequent use. Alternatively, the purified immunoglobulins may be blended immediately with suitable protein sources in a ratio appropriate for the daily intake of the animals for which they are intended. The protein sources might be one or more of the following: skim milk, whey powder, lactalbumin, casein, caseinates and milk co-precipitates. Alternatively, protein products derived from protein sources such as soy meal, fish meal and canola meal might be used. To prepare a porcine immunoglobulin product particularly suited for piglets, the purified immunoglobulins, after the reduction of ammonium sulfate levels, are blended with condensed skim milk to give an appropriate solids ratio, e.g. 1:3 (immunoglobulins/skim milk solids). The resulting mixture is then spray dried to yield a pig-milk replacer component which can be blended with other required constituents, such as protein, fat, minerals, vitamins, reconstituted and fed upon demand. Optionally, addition of fat, minerals and vitamins prior to or after drying gives a complete milk replacer for piglets.

EXAMPLE 1

Figure 2:
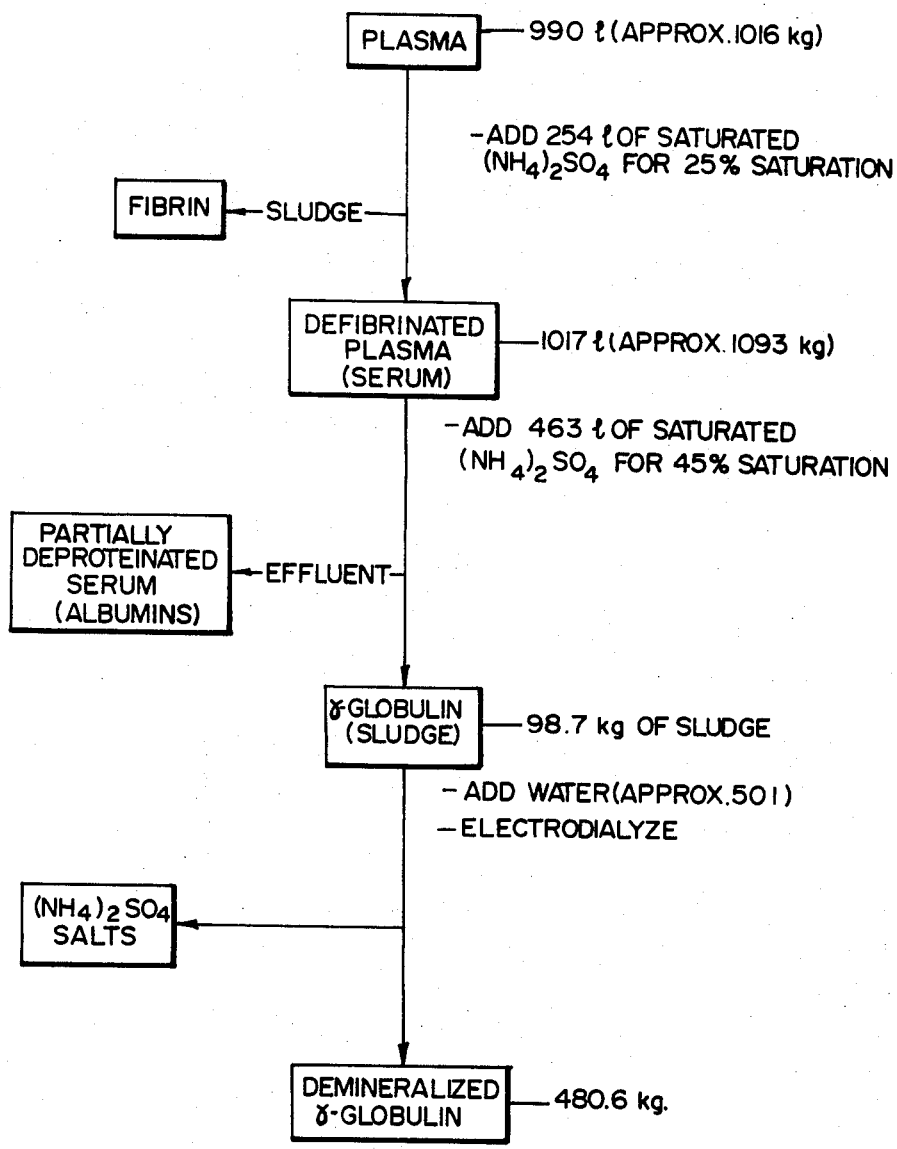
FIG. 2 is a flow diagram for the preparation of purified porcine immunoglobulins according to a specific example.

FIG. 2 summarizes information collected on a major Pilot Plant experiment in which 990 l of plasma (approx. 1016 Kg at S.G. of 1.026) were processed to eventually yield 19.1 Kg of immunoglobulin of 60% purity. In this experiment, 254 l of saturated ammonium sulfate were added to 990 l of plasma to obtain 25% saturation. The precipitate (mainly fibrin) was continuously removed by means of a Westfalia (Trade Mark) clarifier (Model SA7-06) operating at 8380 rpm, a flow of 830 l/hr and a product temperature of 6° C. This yielded 195 Kg of fibrin and 1017 l of defibrinated serum (approx. 1093 Kg at S.G. of 1.075). To this 463.8 l of saturated ammonium sulfate were added to bring saturation to 45% and effect precipitation of the immunoglobulin fraction. This material was subsequently subjected to continuous flow centrifugation using a Pfaudler (Trade Mark) decanting separator (Model Z1L) operating at 5650 rpm with a scroll to bowl differential of +10 rpm and a 140 mm regulating ring to give a 4.6 mm dry beach. During this operation, 98.7 Kg of sludge were recovered and subsequently diluted with water at a rate of approximately 5 l/kg of sludge, in preparation for electrodialysis. This process removed a major portion of the ammonium sulfate previously added.

Electrodialysis was achieved by passing the reconstituted immunoglobulin through a "Stack-Pack" (Trade Mark) unit manufactured by Ionics Inc.. This machine was equipped with 25 cell pairs and electrodialysis was continued until a conductivity of 6 m—mho was obtained: equivalent to about 0.4% ammonium sulfate on a wet basis. In the end, 480.6 Kg of demineralized product were obtained.

Prior art shows that the immunoglobulins account for about 27% of the proteins in blood plasma (Hawk, P. B., et. al. 1954, Practical Physiological Chemistry, 13th Ed., Chapter 22, page 459). Prior art also shows that the solids of blood is 8.51% (±0.2%) of which 6.13% (±0.2%) is total protein (Donnelly, E. B. 1978, Ir. J. Food Sci. & Technology, Vol. 2, pages 31–38). This means that plasma, prior to fibrin removal, contains 27/100 ×6.13 or 1.66% immunoglobulins. From the data in Table 1 it can clearly be seen that the aforementioned continuous process is a powerful means of concentrating the immunoglobulins from 1.66% in the plasma fraction to 13.3% protein in the precipitated immunoglobulin fraction recovered from the decanting centrifuge. This is a 8-fold increase in concentration effected by a single salt system used at two discriminating levels of saturation to preferentially remove fibrin at the 20%–30% level of ammonium sulfate saturation and subsequently precipitate the immunoglobulins at increased saturation levels of 35% to 50% ammonium sulfate. By optimizing the ammonium sulfate saturation levels to preferably, respectively, 25% and 45% saturation, the quantity of protein precipitated can be maximized and the efficiency of the process increased.

The recovery of immunoglobulin by the present process in this example is approximately 78%. This is based on the 1016 Kg of starting plasma containing approximately 1.66% immunoglobulin which represents a mass of 16.8 Kg. As the process is followed through the steps illustrated in FIG. 2, a yield of 98.7 Kg of precipitated immunoglobulin sludge is recovered and contains 13.3% immunoglobulin. The yield of immunoglobulin at this point of 0.133×98.7 Kg or 13.1 Kg. This represents a recovery of 78%. Some additional handling losses can be expected during the deionizing and spray dried stages. Losses of immunoglobulin, due to passage through ultrafiltration (UF) or electrodialysis (ED) membranes, is negligible as the mean diameter of the solvated species is well above maximum size opening in the membrane material. Losses on ion exchange resins can be higher than either ED or UF.

Immunoglobulin prepared by the present process, as illustrated in Example 1, contains low levels of ammonium sulfate as can be seen from the data in Table 2: 2.07% by conductivity and 2.31% by difference. These low levels of residual ammonium sulfate ensure the product will be non-toxic to the pig and will not cause palatability problems in a complete milk replacery.

Products prepared according to the present invention have been analyzed for yeast, mold, Streptococci, Salmonella, thermophilic spores, Staphyloccocci, Coliforms, E. coli and psychrotophs. In addition, they have been also analyzed for pathogenic viruses infective to swine. The results, summarized in Table 3, indicate there are no microbiological hazards associated with production of pig-milk replacer by the present process.

An example of a complete milk replacer formulation for piglets incorporating porcine immunoglobulins, prepared according to the present invention, in skim milk powder is as follows:

| Ingredients | Percentage w/w |
| --- | --- |
| Porcine Immunoglobulins (in skim milk powder) | 14.3 |
| Skim Milk Powder | 47.6 |
| Casein | 8.0 |
| D.L. Methionine | 0.3 |
| Soybean oil | 25.0 |
| Vitamin Premix | 1.0 |
| Trace Mineral Premix | 1.0 |
| Calcium Chloride | 0.17 |
| Emulsifying Agent(s) | 1.2 |
| Lactose | 1.430 |
| | 100.00% |

It should be noted that the amount of skim milk powder in the first ingredient of the preceding example of a complete milk replacer formulation has not been specified. This amount has been intentionally left vague, since that amount of skim milk will vary depending upon the immunoglobulin requirement for the piglet. Once that immunoglobulin requirement is established, then the precise proportion of the spray dried immunoglobulin/skim milk powders component can be readily established by one skilled in the art.

BIOLOGICAL (ANIMAL) TEST

Thirty-six piglets in three replicates were removed from their dams at birth and divided into two groups of 18 (6×3) piglets each and reared artificially until 21 days of age. One group served as a control and received only milk replacer while the second group of 18 received the milk replacer supplemented with immunoglobulins prepared using the process of the present invention. Immunoglobulins were fed at a level of 10 gm/kg body weight on day 1 and 2 gm/kg body weight on days 2–10 inclusive. Thereafter unsupplemented milk replacer was fed. The trial period was 21 days with the following results:

| | Immunoglobulins | |
| --- | --- | --- |
| | 0 | + |
| No. of pigs started | 18 | 18 |
| No. of pigs surviving to 21 days | 7 | 14 |
| % Mortality | 61.1 | 22.2 |
| Average daily gain (gm) | 100 | 140 |

The level of survival amongst control pigs (38.9%) was unusually high although not unexpected given the minimal disease status of the experimental unit in which the test was carried out. However, the survival amongst pigs supplemented with immunoglobulin prepared by the processed process (77.8%) was significantly greater and due to the presence of the immunoglobulin supplements.

The present invention provides, for the first time, a continuous flow process which makes the production of immunoglobulin products feasible on a commercial (plant) size operation.

EXAMPLE 2

Figure 3:
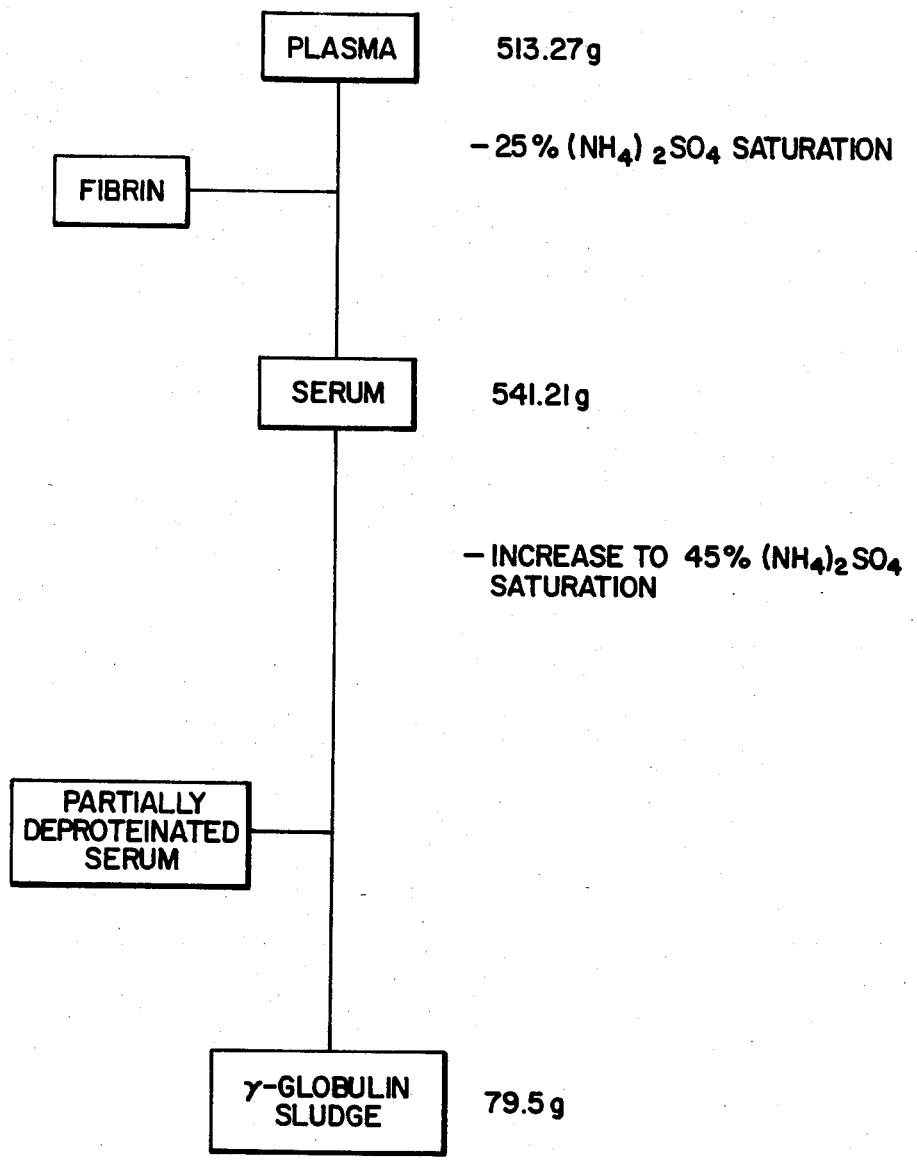
FIG. 3 is a flow diagram for the preparation of bovine immunoglobulins according to a specific example.

Bovine immunoglobins were fractionated in a similar manner as previously reported for porcine immunoglobins in Example 1. Bovine blood was collected, preserved and centrifuged to remove red blood cells yielding 513.27 g of plasma containing approximately 1.66% of immunoglobin which represents a mass of 8.5 g immunoglobin. FIG. 3 is a flow diagram illustrating the process which was carried out on the resultant plasma. The yield of immunoglobin sludge was 79.5 g containing 34.3% solids to give a solids yield of 27.3 g. This product was analyzed and found to contain 38.9% protein. Electrophoresis revealed that this protein contained 62.6% immunoglobin. Therefore the resulting yield of immunoglobin was (27.3×0.389×0.626=) 6.6 g. This represents a yield (6.6/8.5) of 77.6% equivalent to the 78% yield for porcine immunoglobin in Example 1. Thus, it is apparent that equivalent yields of bovine immunoglobulin can be achieved using this process.

In conclusion it is apparent that there has been provided in accordance with the invention a method for the continuous production of a purified immunoglobulin preparation that fully satisfies the objects, aims and advantages set forth above. While the invention has been described in conjunction with a specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

TABLE 1

Analytical data for solids, ash and protein on various fractions during the preparation of immunoglobulin enriched pig-milk replacer component.

| Fraction | Wt. (Kg) | Solids (%) | Ash (%) | Total Protein (%) | Total Immunoglobulin (%) |
|---|---|---|---|---|---|
| Plasma | 1016 | 8.51 (±.2)$^a$ | — | 6.13 (±.2)$^a$ | 1.66$^b$ |
| Serum | 1093 | 5.85 | .12 | 3.39 | — |
| Ppt. Immunoglobulin$^c$ | 98.7 | 38.70 | .68 | 22.16 | 13.3 |
| Reconstituted Immunoglobulin$^d$ | — | 6.25 | .11 | 5.33 | — |
| Electrodialyzed Immunoglobulin$^d$ | 480.6 | 4.11 | .03 | 3.98 | — |
| Condensed Skim Milk | — | 36.2 | 2.98 | 13.63 | — |
| Immunoglobulin Skim Milk Mixture$^d$ | — | 10.71 | .74 | 5.96 | 1.6 |
| Spray Dried Immunoglobulin Skim Milk Mixture$^{d,\,e}$ | — | 94.65 | 5.98 | 48.76 | 14.6 |

$^a$Data from Donnelly, Irish J. of Food Sci. & Technology, 1978. Vol. 2, Pages 31–38.
$^b$Data from Hawk et. al. 1954. Practical Physiological Chemistry, 13th Edition, Chap. 22. - Page 459.
$^c$Average of two values.
$^d$Average of six values.
$^e$Mixed 3 parts condensed skim milk with 1 part electrodialyzed immunoglobulins and spray dried.

TABLE 2

Analysis of pig-milk replacer component prepared according to Example 1 (75% skim milk solids and 25% immunoglobulins) after spray drying.$^a$

| Total Protein Nitrogen | Total Nitrogen (%) | Total NPN Nitrogen (%) | NPN Contribution$^b$ (NH$_4$)$_2$SO$_4$ (%) | NPN Contribution$^b$ Milk (%) | (NH$_4$)$_2$SO$_4$ in Final Product (%) By Conductivity | (NH$_4$)$_2$SO$_4$ in Final Product (%) By Difference |
|---|---|---|---|---|---|---|
| 7.64 (48.76% protein) | 8.22 | .58 | .49 | .09 | 2.07 | 2.31 |

$^a$Average of five values.
$^b$NPN - non-protein nitrogen

TABLE 3

Microbiological analysis of immunoglobulin enriched pig-milk replacer component

| Organism | Log$_{10}$ Maximum Number Reported |
|---|---|
| Total bacteria | 4.97 |
| Yeast | 2.93 |
| Mold | 1.74 |
| Yeast & Mold | 2.93 |
| Streptococci | 2.97 |
| Psychrotrophs | 3.86 |
| Salmonella | negative |
| Thermophilic spores | negative |
| Most Probable number/g | |
| Staphlococci | 9.1 |
| Coliforms (confirmed) | 36 |
| E. coli | 3.6 |
| Influenza virus | negative |
| TGE virus | negative |
| HEV virus | negative |

What we claim as our invention:

1. A method of continuous production of an animal feed component containing purified immunoglobulins, the method comprising the sequential steps of:
    (a) adding an anti-coagulant to collected blood to prevent the formation of fibrin;
    (b) centrifugally removing from the blood the cellular fractions;
    (c) adding ammonium sulfate to the remaining plasma to obtain a first stage ammonium sulfate saturation of approximately 20% to 30% to induce fibrin precipitation;
    (d) removing the precipitated fibrin by subjecting the plasma to continuous centrifugation;
    (e) increasing the ammonium sulfate saturation of the remaining defibrinated plasma to a second stage ammonium sulfate range of approximately 35% to 50%;
    (f) subjecting the defibrinated plasma to further continuous centrifugation to separate the soluble albumins from the precipitated globulins;
    (g) collecting the continuously discharged immunoglobulin-containing sludge from this centrifugation step and adding water to redissolve therein the immunoglobulins;
    (h) subjecting the aqueous immunoglobulin solution to an ion depletion process to remove a major portion of the ammonium sulfate; and
    (i) blending the purified immunoglobulin material from step (h) while still in aqueous form with a suitable protein source in a ratio appropriate for the daily intake of an animal to which it is to be fed.

2. A method according to claim 1 wherein the collected blood is porcine.

3. A method according to claim 1 wherein the purified aqueous immunoglobulin recovered from step (h) is blended with a protein source selected from the group consisting of skim milk, whey powder, lactalbumin, casein, caseinates and milk co-precipitates.

4. A method according to claim 3 wherein the purified aqueous immunoglobulin material obtained from step (h) is blended with condensed skim milk to give a solids ratio of about 1:3 (immunoglobulins/skim milk solids), and the resulting mixture is spray dried to yield a pig-milk replacer component which can be reconstituted and fed as required.

5. A method according to claim 4 wherein fat, protein, minerals and vitamins are added to the product prior to or after spray drying to give a complete milk replacement.

6. A method according to claim 4 wherein the anticoagulant is sodium citrate.

7. A process according to claim 4 wherein ammonium sulfate is added to the plasma to obtain a saturation of 20% to 30% in a batch system or portion metered in-stream on a continuous flow basis.

8. A process according to claim 4 wherein ammonium sulfate is increased to a concentration in the range of 35% to 50% by addition of ammonium sulfate in a batch system or portion metering in-stream on a continuous flow basis.

9. A process according to claim 4 wherein the immunoglobulin solution is subjected to an ion depletion process selected from the group consisting of ion exchange, diafiltration, ultrafiltration or electrodialysis.

10. A process according to claim 4 wherein the ammonium sulfate concentration is increased to approximately 25% in the first stage of ammonium sulfate saturation.

11. A process according to claim 10 wherein the ammonium concentration is increased to approximately 45% in the second stage of ammonium sulfate saturation.

12. A method according to claim 1 wherein the collected blood is bovine.

13. A method of continuous production of a pig-milk replacer component which can be reconstituted and fed to piglets as required, comprising the sequential steps of:
   (a) adding an anti-coagulant to collected porcine blood to prevent the formation of fibrin;
   (b) centrifugally removing from the blood the cellular fractions;
   (c) adding ammonium sulfate to the remaining plasma to obtain a first stage ammonium sulfate saturation of approximately 20% to 30% to induce fibrin precipitation;
   (d) removing the precipitated fibrin by subjecting the plasma to continuous centrifugation;
   (e) increasing the ammonium sulfate saturation of the remaining defibrinated plasma to a second stage ammonium sulfate range of approximately 35% to 50%;
   (f) subjecting the defibrinated plasma to further continuous centrifugation to separate the soluble albumins from the precipitated globulins;
   (g) collecting the continuously discharged immunoglobulin-containing sludge from this centrifugation step and adding water to redissolve therein the immunoglobulins;
   (h) subjecting the aqueous immunoglobulin solution to an ion depletion process to remove a major portion of the ammonium sulfate;
   (i) blending the purified aqueous immunoglobulin material obtained from step (h) with condensed skim milk in a ratio appropriate for the daily intake of an animal to which it is to be fed; and
   (j) spray drying the resulting mixture to yield a pig-milk replacer component which can be reconstituted with aqueous liquid and fed as required.

14. A method according to claim 13 wherein fat, protein, minerals and vitamins are added to the product prior to or after spray drying to give a complete milk replacement.

15. A method according to claim 13 wherein the purified acqueous immunoglobulin material from step (h) is blended with condensed skim milk to give a solids ratio of about 1:3 (immunoglobulins/skim milk solids).

* * * * *